United States Patent
Bankowski

(10) Patent No.: US 10,538,474 B2
(45) Date of Patent: Jan. 21, 2020

(54) METHOD OF PRODUCING HIGH-PURITY MONOCHLOROACETIC ACID

(71) Applicant: PCC MCAA SP. Z O.O., Brzeg Dolny (PL)

(72) Inventor: Bartosz Bankowski, Wroclaw (PL)

(73) Assignee: PCC MCAA SP. Z O. O., Brzeg Dolny (PL)

(*) Notice: Subject to any disclaimer, the term of this patent is extended or adjusted under 35 U.S.C. 154(b) by 0 days.

(21) Appl. No.: 16/074,468

(22) PCT Filed: Feb. 4, 2017

(86) PCT No.: PCT/PL2017/050007
§ 371 (c)(1),
(2) Date: Aug. 1, 2018

(87) PCT Pub. No.: WO2017/135833
PCT Pub. Date: Aug. 10, 2017

(65) Prior Publication Data
US 2019/0062252 A1  Feb. 28, 2019

(30) Foreign Application Priority Data

Feb. 4, 2016  (PL) .......................... 416028

(51) Int. Cl.
| C07C 51/363 | (2006.01) |
| C07C 51/377 | (2006.01) |
| C07C 51/44  | (2006.01) |
| C07C 51/487 | (2006.01) |
| B01D 3/10   | (2006.01) |

(52) U.S. Cl.
CPC .............. *C07C 51/363* (2013.01); *B01D 3/10* (2013.01); *C07C 51/377* (2013.01); *C07C 51/44* (2013.01); *C07C 51/487* (2013.01)

(58) Field of Classification Search
None
See application file for complete search history.

(56) References Cited

U.S. PATENT DOCUMENTS 2,539,238 A * 1/1951 Eaker .................... C07C 51/363
                                                         560/226
2,688,634 A    9/1954 Pinkston, Jr.
(Continued)

FOREIGN PATENT DOCUMENTS

| CN | 102274708 A | 12/2011 |
| CN | 104649887 A | 5/2015  |

(Continued)

OTHER PUBLICATIONS

International Search Report and Written Opinion issued in corresponding International Patent Application No. PCT/PL2017/050007 dated May 31, 2017 (8 pages).

*Primary Examiner* — Amy C Bonaparte
(74) *Attorney, Agent, or Firm* — Kilyk & Bowersox, P.L.L.C.

(57) ABSTRACT

A method has been disclosed of obtaining high purity, colourless monochloroacetic acid encompassing the chlorination of acetic acid with chlorine in the presence of a catalyst, followed by the recovery of the catalyst through vacuum distillation and purification of the obtained liquid raw product by its hydrodehalogenation by hydrogen in the presence of a palladium catalyst and then vacuum distillation.

12 Claims, 3 Drawing Sheets

(56) References Cited

U.S. PATENT DOCUMENTS

| | | | |
|---|---|---|---|
| 5,756,840 A | | 5/1998 | Ebmeyer et al. |
| 2005/0272953 A1 | | 12/2005 | Crouzen et al. |
| 2014/0275625 A1 | * | 9/2014 | Nieuwhof ............ C07C 51/487 562/604 |

FOREIGN PATENT DOCUMENTS

| | | | |
|---|---|---|---|
| CN | 105130786 A | | 12/2015 |
| CN | 106242961 A | | 12/2016 |
| DE | 910778 | * | 5/1954 |
| NL | 109769 C | | 10/1964 |
| WO | 2013057125 A1 | | 4/2013 |
| WO | 2017135832 A1 | | 8/2017 |

* cited by examiner

METHOD OF PRODUCING HIGH-PURITY MONOCHLOROACETIC ACID

This application is a National Stage Application of PCT/PL2017/050007, filed Feb. 4, 2017, which claims priority to Polish Patent Application No. P.416028, filed Feb. 4, 2016.

The subject matter of the invention is an improved method of producing monochloroacetic acid (MCAA), in which a colourless high-purity product is obtained. The method according to the invention is used for the industrial production of essentially colourless MCAA.

Derivatives of monochloroacetic acid, MCAA, are currently used in many branches of industry, including in the food industry, for producing thickeners, in the cosmetics industry, for instance in the production of shampoos or personal care products and the paint industry for producing artificial dyes and pigments. It is also used in the production of medicines, analgesics and vitamin B6. Monochloroacetic acid is also a raw material that is widely used in the drilling industry, where its derivatives are used for water-bonding agents, such as in the case of bore holes related to shale gas exploration.

The increase in the consumption of monochloroacetic acid (MCAA) in the production of pharmaceuticals and derivatives used in cosmetics is also resulting in an increase in demand for very high purity MCAA, not only regarding dichloroacetic acid content, which is the most sensitive impurity, but also in terms of colour.

Therefore, industrial MCAA production technology is constantly being developed to increase its efficiency, reduce raw material losses and extend the lifetime of the heterogeneous catalysts used in the purification processes.

The method of producing raw monochloroacetic acid most commonly used in industry is direct chlorination of acetic acid with chlorine gas in the presence of a homogeneous catalyst at increased pressure:

$$CH_3COOH+Cl_2=CH_2ClCOOH+HCl$$

The reaction usually takes place in a reactor in the liquid phase at a pressure of 3-5 barg. The reaction mixture is saturated with chlorine gas, which is dissolved in the liquid phase, in waterless conditions. The catalysts in the process are acetyl chloride ($CH_3COCl$) and chloroacetyl chloride ($ClCH_2COCl$), which are usually formed in-situ from acetic anhydride, which is added precisely because it is a precursor of acid chlorides. Hydrogen chloride is produced during the reaction. HCl causes the conversion of the anhydride to acid chloride and acetic acid. The following reactions take place during chlorination:

$$(CH_3CO)_2O+HCl=CH_3COOH+CH_3COCl$$
(formation of acetyl chloride)

$$CH_3COCl+Cl_2=ClCH_2COCl+HCl$$
(reaction of acetyl chloride with chlorine to chloroacetyl chloride)

$$ClCH_2COCl+CH_3COOH=ClCH_2COOH+CH_3COCl$$
(reaction of chloroacetyl chloride to MCAA)

$$ClCH_2COCl+Cl_2=Cl_2CHCOCl+HCl$$
(formation of dichloroacetyl chloride)

$$ClCH_2COCl+ClCH_2COOH=Cl_2CHCOOH+CH_3COCl$$
(reaction of MCAA and acetyl chloride to dichloroacetic acid)

$$Cl_2CHCOCl+CH_3COOH=Cl_2CHCOOH+CH_3COCl$$
(formation of DCAA from dichloroacetyl chloride)

$$ClCH_2COOH+Cl_2CHCOCl=Cl_2CHCOOH+ClCH_2COCl$$
(reaction of MCAA with dichloroacetyl chloride to DCAA).

A number of other (mixed) anhydrides are also formed during the acetic acid chlorination process. Therefore, the mixture will contain acetic anhydride, acetic-chloroacetic anhydride and mixed MCAA and DCAA anhydrides. All of these anhydrides will react with hydrogen chloride to produce acids and acid chlorides.

In the conditions of the chlorination process, the reaction of the acid anhydrides with hydrogen chloride does not take place until the end because a state of equilibrium is being formed. For this reason, acetic anhydride and other anhydrides are present in the mixture feeding the unit process following chlorination, namely the recovery of the chlorination catalyst.

After separation from the rest of the process mixture through distillation or stripping with hydrogen chloride, the chlorides are returned to the chlorination process. The higher the degree of recovery of acid chlorides, the lower the requirement for acetic anhydride in the chlorination process.

The recovery of the catalyst through stripping with hydrogen chloride enables the recovery of the most of chlorides, although this method requires the process to be conducted under increased pressure (WO 2013057125) so as to move the chlorides—acid anhydrides equilibrium towards the chlorides and to enable them to be blown away using hydrogen chloride gas. This method is problematic because of the need to maintain absolute tightness of the apparatus and reduces the degree of evaporation of chlorides from the mixture. Although anhydrides more easily change into chlorides and the mixture directed to hydrogenation contains virtually no anhydrides, it is difficult to introduce chlorides from the system in the form of gaseous effluent, while the process equipment is exposed to much faster wear and tear. As a result, however, some of the anhydrides, which were introduced to the stripping column together with the process liquid, will be present in the liquid feeding the hydrodehalogenation process.

The use of the distillation process for recovering the catalyst under reduced pressure is a much better solution for the maintenance of the installation. Such a distillation process should be ensured so that the majority of chlorides evaporate immediately upon entering the column (flash feed) and therefore are unable to condense and change into anhydrides due to the large excess of acids. Of course, a small proportion of chlorides will remain in the column and will react with the appropriate anhydrides. Anhydrides, which were originally present in the reaction mixture, also find their way to the bottom of the distillation column.

Since dichloroacetic acid (DCAA), which is the most unwanted by-product, is also contained in the reaction mixture from the chlorination process, the next stage of the production process is the removal of the product of this contamination. DCAA may be removed from the reaction mixture by distillation, crystallization or hydrodehalogenation (hydrogenation).

DCAA has a similar boiling point to MCAA and the removal of this impurity using distillation is uneconomic. It is also difficult to reduce the level of DCAA through crystallization in industrial environments. The level of DCAA contamination, which is admissible in most applications, lying within the range of 100 to 500 ppm, would require the use of an equally uneconomic operation of multi-stage crystallization. In both cases, it would be necessary to deal with the problems of disposing of this unwanted by-product.

A well-known and commonly used method of removing DCAA from the raw product is to conduct catalytic hydrodehalogenation in the presence of a heterogeneous palladium catalyst. This process can be conducted in both the gas and liquid phase, whereby the catalyst may be in the form of a fixed bed or a suspension. The hydrodehalogenation process is currently the most efficient method of purifying MCAA of DCAA.

Unfortunately, the acid chlorides and acid anhydrides described above are transformed in the hydrodehalogenation process into undesirable colouring products, usually polymerizing and sealing the pores of the catalyst and depositing on the inner surfaces of the apparatus, thereby reducing its performance in subsequent unit processes. Acid chlorides are simultaneously an inhibitor of the hydrogenation catalyst.

Therefore, the presence of both chlorides and anhydrides during hydrogenation will result in the generation of waste, as well as a reduction in the efficiency of the production process and an increase in raw material consumption. It can also cause a deterioration of the colour of the final product.

The MCAA production process is typically conducted in such a way that the mixture which is sent to hydrodehalogenation is exposed to small amounts of water immediately after the stage of recovering the chlorination catalyst (stripping the chlorides with hydrogen chloride gas), which causes the immediate hydrolysis of the acid chlorides (NL 109 769 C, 1964) giving an appropriate acid and hydrogen chloride. However, this method is so imperfect that the addition of water in stoichiometric quantities is only able to destroy the acid chlorides. A relatively large surplus of water is required to destroy the anhydrides because of the kinetics of their hydrolysis.

However, it should be remembered that an excessively high concentration of water will have a negative impact on the course and efficiency of the hydrogenation process because the water in the reaction with the MCAA gives glycolic acid, which, in turn, tends to create esters, which also make up heavy fractions which reduce the efficiency and selectivity of the process.

The authors of patent application WO 2013057125 propose removing the residual chlorides and/or anhydrides from the mixture after the chloride recovery stage, but before the hydrodehalogenation stage, by adding such a quantity of water to the stream of process fluid flowing from the chloride recovery unit to the hydrodehalogenation, which, after the reaction of the chlorides and possibly anhydrides, results in the concentration of water being between 0.01 and 5% by weight of water.

However, it arises from WO 2013057125 that the colour of the MCAA obtained lies within the range of 20 to 100 units on the Pt—Co scale.

Furthermore, in accordance with WO 2013057125, a mixture of chloroacetic acid, dichloroacetic acid and possibly acetic acid containing a specified quantity of water (no more than 5%) is sent to the hydrodehalogenation process, the presence of which during the hydrodehalogenation process, contrary to the suggestions contained in the state of the art, still causes the emergence of glycolic acid, which then, in turn, reacts into esters.

During distillation, the glycolic acid and its derivatives are condensed further, thereby giving heavy polymeric fractions. As a further downside, the heavy fractions arise under the influence of high temperature as early as during the hydrodehalogenation process, which, in the longer term, results in the degradation of the performance of the catalytic beds (see comparative example below).

Furthermore, the authors of application WO 2013057125 claim that the concentration of the water after the hydrolysis stage should be within the range of 0.01-5% by weight without specifying the time in which hydrolysis takes place. Hydrolysis of anhydrides is a process which requires an appropriate time for reaction under the assumption that the mixture contains an appropriate excess of water with respect to the content of anhydrides. The solution described in WO 2013057125 does not provide for an appropriate time for the reaction of the water with the anhydrides if they are present in the stream for hydrogenation. The authors of this application emphasize that the anhydrides which are present before adding the water are present in the mixture directed to the hydrodehalogenation. This creates a risk that if anhydrides are present in the stream before hydrolysis (the addition of water), both anhydrides and a significant excess of water will be present in the stream for hydrodehalogenation, which will result in the emergence of additional quantities of unwanted by-products.

Since, in addition to acid chlorides, acid anhydrides and water are also causes of the emergence of impurities such as aldehydes, products of the aldol condensation of aldehydes, glycolic acid and its derivatives, as well as heavy organic fractions, which have an adverse impact on the performance of unit processes and the life time of the hydrodehalogenation catalyst, special attention should be paid to the elimination of not only chlorides from the liquid feeding the hydrodehalogenation process, but also anhydrides, while keeping the process mixture as anhydrous as possible.

OBJECTIVE OF THE INVENTION

Figure 1:
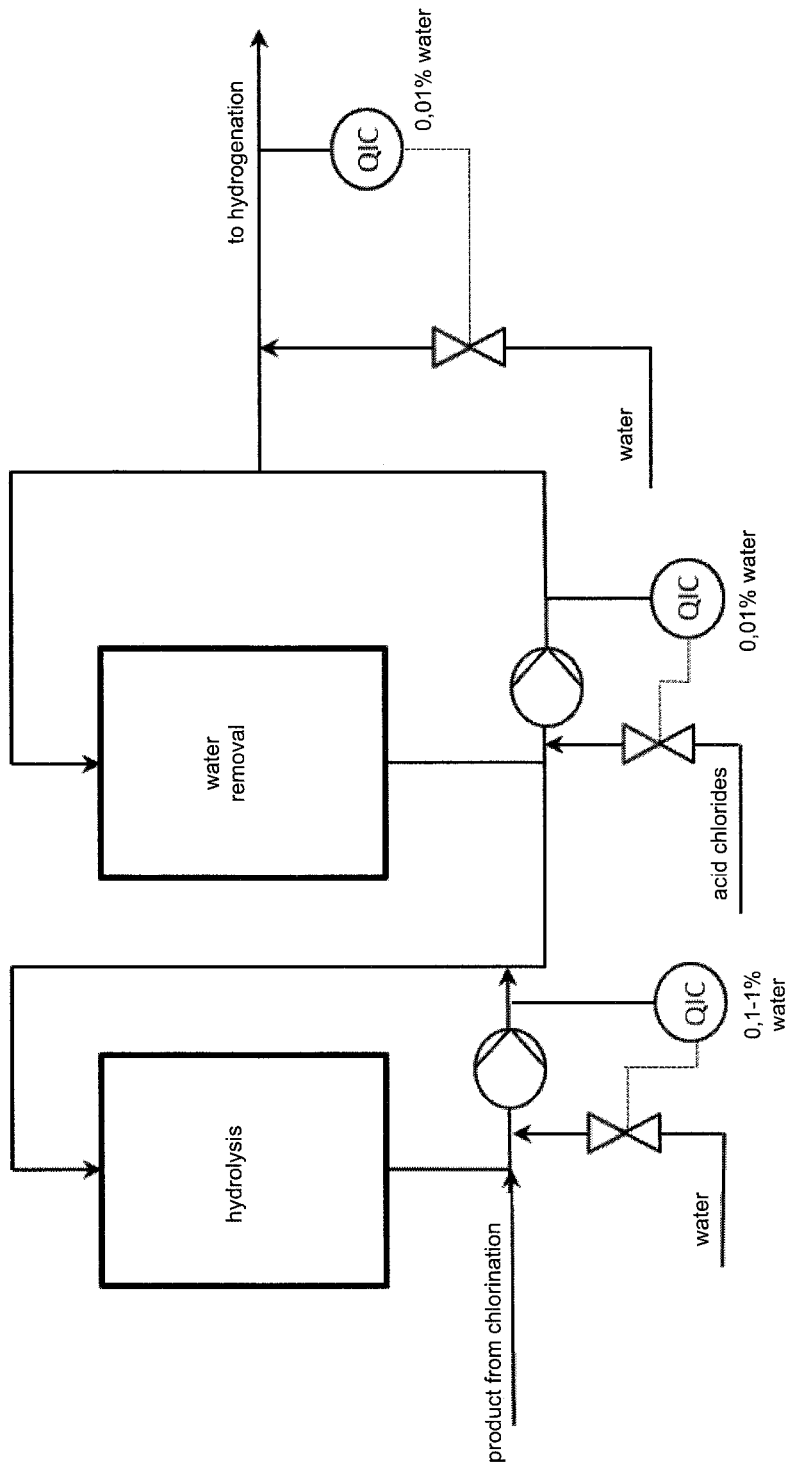
FIGS. 1 and 2 are diagrams each showing processes of hydrodehalogenation of the present invention.

The objective of the invention is to provide a method of industrially obtaining ultra-pure MCAA, preferably of a colour not exceeding 10 units on the Pt—Co scale, as well as avoiding the contamination of the product stream after hydrodehalogenation with impurities which give rise to the risk of polymerization; in particular, it is desirable for the product stream after hydrodehalogenation to contain no more than 0.08% GAMA and less than 100 ppm glycolic acid.

In order to eliminate anhydrides from the process mixture, an amount of water corresponding to the stoichiometry should be applied and the reaction time should be extended theoretically to infinity, or an appropriate excess of water should be applied enabling the relatively fast reaction of the anhydrides.

Essence of the Invention

The objective unexpectedly defined above has been achieved in a manner according to the invention.

The subject matter of the invention is the method of obtaining high purity, colourless monochloroacetic acid encompassing the chlorination of acetic acid with chlorine in the presence of a catalyst, followed by the recovery of the catalyst through vacuum distillation and purification of the remaining liquid raw product by its hydrodehalogenation in the presence of a palladium catalyst and then vacuum distillation characterized by the fact that a. anhydrides and acid chlorides which are present in the stream of the liquid product obtained after the stage of recovery of the catalyst are hydrolysed, whereby hydrolysis is conducted with such a continuous excess of water with respect to the content of chlorides and anhydrides that the concentration of water in the mixture leaving to the next stage is between 0.05 and 5% by weight, in a temperature of between 50 and 160° C. and then b. the excess water is removed by a reaction with acid chlorides so that the concentration of water in the reaction mixture entering the hydrodehalogenation process is less than 2%.

The hydrolysis of the anhydrides and acid chlorides is preferably conducted in the reactor or an intermediate tank or in a cascade of reactors with an overall retention time of between 30 minutes and 12 hours.

The concentration of water in the reaction mixture entering the hydrodehalogenation process is preferably less than 1% by weight, preferably less than 0.01% by weight.

Hydrodehalogenation is preferably conducted by the action of hydrogen gas on the raw product in the presence of a catalyst containing metal from group X of the periodic table of elements, preferably palladium or platinum.

The catalyst is preferably deposited on a carrier in the form of powder, granules or extrusions of activated carbon, silica or zeolite.

The hydrodehalogenation process preferably takes place in the liquid or gaseous phase.

The hydrodehalogenation process is preferably conducted in the liquid phase in a reactor with a fixed catalyst bed.

The hydrodehalogenation process is preferably conducted in the liquid phase in a circulation reactor.

The hydrodehalogenation process is preferably conducted in the gaseous phase in a reactor with a fixed catalyst bed.

The reactor or cascade of reactors, in which the hydrolysis of the anhydrides is conducted, preferably enables the liquid in it to mix.

During the stage of hydrolysis of the anhydrides, the excess water is preferably within the range of 0.2 to 5% by weight.

In another embodiment, during the stage of hydrolysis of the anhydrides, the excess water is preferably within the range of 0.3 to 0.7% by weight.

The essence of the invention lies in the fact that an excess of water with respect to the content of chlorides and anhydrides is added to the process liquid after the stage of recovering the chlorination process catalyst, after which such a mixture is sent to the intermediate tank, in which the anhydrides are hydrolysed as a result of the appropriate surplus of water, high temperature, appropriate retention time and appropriately strong mixture. Next, the excess water is removed completely through the addition of acid chlorides to the stream supplying the hydrodehalogenation node.

Figure 2:
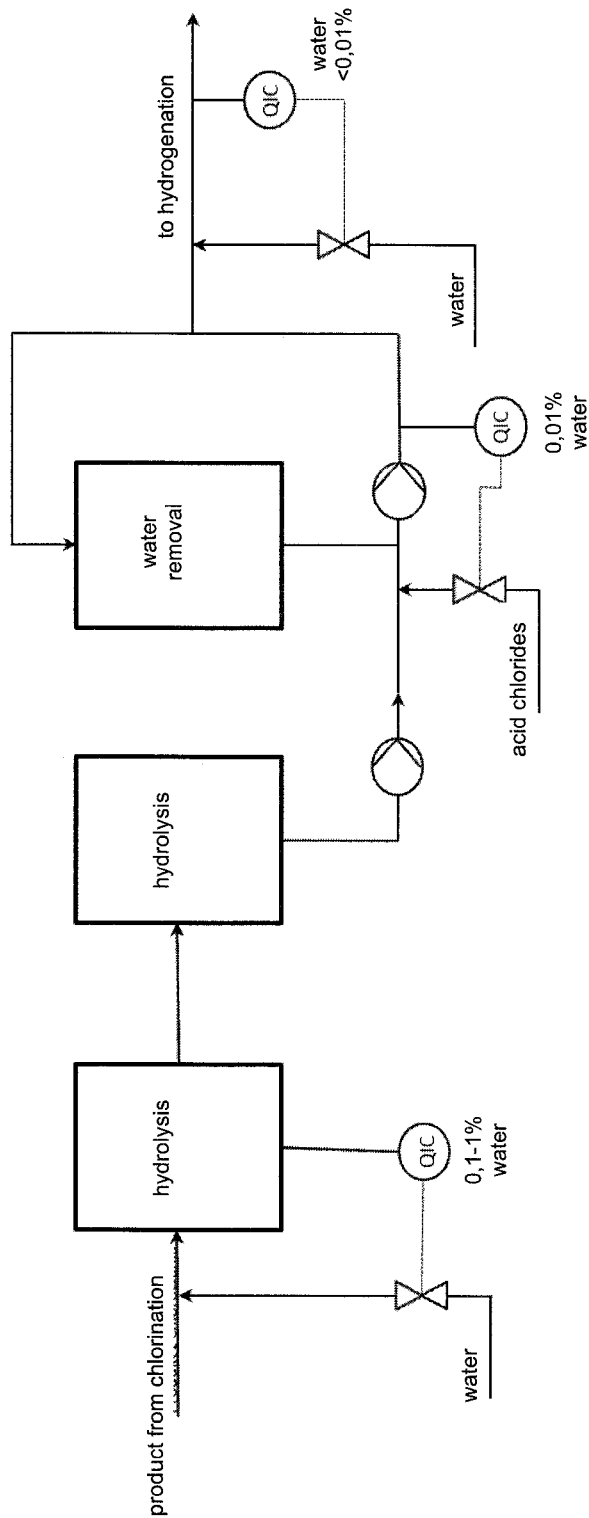

The chlorides, which have undergone hydrolysis, must be supplemented with the addition of acetic anhydride to the acetic acid chlorination process. In order to minimize the consumption of acetic anhydride, the excess water in the first phase must be kept at a minimum level which however, must enable the hydrolysis of all the anhydrides in the intermediate tank. This is achieved with the use of an appropriate size of intermediate tank in which the reaction of the anhydrides and the water takes place. Either a single tank of an appropriate size or a cascade of two or more reactors can be used to hydrolyse the anhydrides. The use of a cascade leads to a reduction in the volume required to conduct the reaction or a reduction in the required excess of water (FIGS. 1 and 2).

Figure 3:
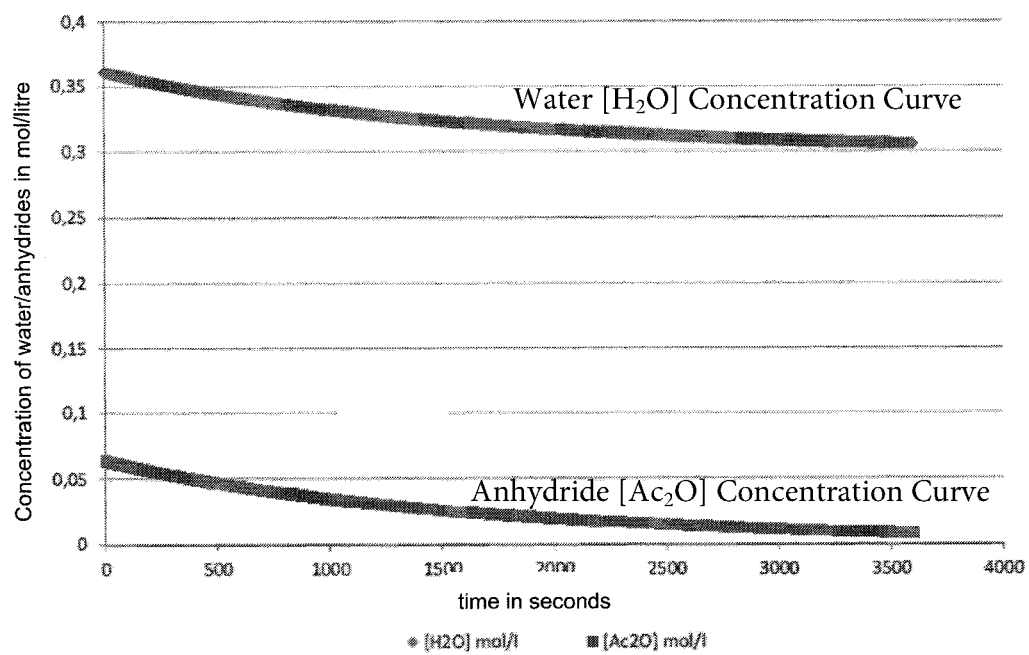
FIG. 3 is a graph plotting concentration of anhydrides versus time and plotting concentration of water versus time for kinetic calculations of the acetic anhydride hydrolysis process from the present invention.

The kinetic calculations of the acetic anhydride hydrolysis process show that, in the case of a concentration of anhydrides at a level of 0.05 mol/dm$^3$ (approx. 0.5% by weight), it is sufficient to maintain the concentration of water in the intermediate tank at a level of up to 0.5 mol/dm$^3$ (0.09% by weight) to achieve the almost total reaction of anhydrides, assuming that the retention time is approximately 1 hour and the process temperature is 120° C. (FIG. 3).

After hydrolysis of the anhydrides, the excess water is destroyed by adding an appropriate quantity of acid chlorides to the process liquid. After the reaction, the concentration of the water must be as low as possible and must be less than 0.01% by weight, because the water also causes the formation of polymeric fractions during hydrodehalogenation. It is also important that the amount of chlorides added is no greater than the amount of water contained in the mixture after the hydrolysis stage.

If an excessive quantity of chlorides has been added to the system, they could enter the hydrodehalogenation reactors. In turn, if there is an insufficient quantity of chlorides, water would be found in the mixture for hydrogenation. For this reason, an additional point is required for measuring the concentration of water and for appropriately securing the system with locks cutting off the supply of process liquid to the hydrogenation node if the concentration of water exceeds 100 ppm and if chlorides appear in this mixture. Therefore, the hydrogenation node may be fed from a buffer tank positioned between the shut-off valve, which is closed as a result of exceeding the admissible concentration of chlorides or water, and the hydrodehalogenation reactors. Such a configuration enables the maintenance of continuity of the hydrodehalogenation process in unexpected failure conditions of the installation, in which the concentration of one of the undesirable components of the mixture feeding into the hydrogenation node increases.

EXAMPLE 1. (COMPARATIVE EXAMPLE)

A reaction mixture from the chlorination of acetic acid with chlorine gas has been analysed without derivatization by gas chromatography with a flame ionization detector (GC-FID) and HPLC. The composition of the mixture is 68% MCAA, 4.5% DCAA, 21.2% acetic acid and 2.6% acetyl chloride, 1.8% chloroacetyl chloride, 1.2% acetic anhydride and 0.7% hydrogen chloride. The mixture was subjected to gas stripping with hydrogen chloride to separate the acid chlorides. To achieve this, the mixture was fed into the top of the stripping column at a flow rate of 3 kg/h. At the same time, hydrogen chloride gas was fed into the column from the bottom. The pressure in the process was 2.5 bar (a) and the temperature was 130° C. The flow of hydrogen chloride was set at 1.5 kg/h.

The mixture at the exit from the stripping column contained 71.9% MCAA, 4.8% DCAA, 21.6% acetic acid and 0.2% acetyl chloride, 0.3% chloroacetyl chloride, 0.3% acetic anhydride and 0.9% HCl. The product obtained after stripping was passed through a static mixer at a rate of approximately 3 kg/h, into which water was also dosed in quantities of 100 g/h, after which the mixture containing water was directed to the hydrodehalogenation process. The hydrodehalogenation system was equipped with a thermally insulated column reactor filled with a heterogeneous catalyst (1% palladium on granular activated carbon). The volume of the catalyst bed was 6 litres, while its height was 3 m. The mixture leaving the column in which water was mixed was continuously dosed at the top of the hydrodehalogenation column. The GC-FID and HPLC analysis of the mixture after adding water, but before hydrogenation showed that this mixture contains 72.3% MCAA, 4.8% DCAA, 18.9% acetic acid, 0.2% acetic anhydride and 0.6% HCl, as well as 3.2% water.

The hydrodehalogenation process was conducted continuously at a temperature of 140° C., measured at the top of the column for 72 hours. The reactor was supplied from the bottom with hydrogen in a quantity of 120 Nm$^3$/h. After a single passage through the column, the mixture contained 0.9% DCAA. The HPLC and GC-FID analyses found the presence of an ester of chloroacetic and glycolic acid (GAMA) in a quantity of 0.9% and glycolic acid (GA) in a quantity of 0.4% in the product after hydrogenation.

The reaction mixture after hydrogenation was yellow, while the gaseous effluents from the hydrodehalogenation stage passing through the alkaline scrubber removing hydrogen chloride coloured the solution yellow. Minimal quantities of acetaldehyde (120 ppm) were found in the reaction mixture, but it was not possible to precisely measure the concentration of this compound because of its volatility and reactivity.

The mixture was subjected to vacuum distillation after hydrodehalogenation, at which stage acetic acid was distilled off. The distillation was repeated to distil off pure monochloroacetic acid. The product (MCAA) was collected as a colourless distillate. The colour on the Pt—Co scale was 10 units. Distillation was stopped when the residue in the column bottom blocked further operation and the distillate started to take on a yellow colour. 11 kg of a tar-like substance, of a content of approximately 45% MCAA was obtained as a residue of the distillation. The rest was polymeric fraction, the composition of which was not analysed. The ratio of the quantity of heavy residues to the quantity of product received is 0.051.

EXAMPLE 2

A sample of a mixture of a composition as in the case of the mixture used in example 1 was subjected to the distillation process under reduced pressure in order to recover volatile fractions containing acid chlorides. After distillation, the mixture had the following composition: MCAA 75.1%, DCAA 5.2%, AcOH 17.0%, acetyl chloride 0.2%, chloroacetyl chloride 0.4%, acetic anhydride 1.9% and HCl 0.2%. A mixture of this composition was passed through a static mixer at a flow rate of approximately 3 kg/h, into which water was also dosed in quantities of 30 g/h, after which the mixture containing water was taken to the container with an agitator of an operating volume of 7 litres. After two hours of hydrolysis, a sample was taken and the mixture was analysed for water content. It was found that the concentration of water was 0.54%. Next, the process mixture from the hydrolysis tank started to be added continuously to the receiver, which was equipped with an agitator and outlet for gaseous effluent, keeping a constant level of liquid in the hydrolysis tank. The hydrolysis time was 2 hours, while a temperature of 130° C. was maintained in the tank. The mixture's water content was determined at the end of the hydrolysis. The concentration of water was 0.53%, whereby no presence of acid chlorides and anhydrides was found in the water. The mixture in the receiver was treated with acetyl chloride in a quantity of 23.6 g/kg of liquid and the water and acetyl chloride content were determined after thorough mixing. The water content was 60 ppm, while no presence of acid chlorides was found. Next, liquid started to be added for hydrodehalogenation in the same way and under the same conditions as in example 1.

The product obtained from hydrodehalogenation was straw-coloured, which is related to the formation of negligible quantities of acetaldehyde. However, the product contained only 0.015% GAMA and less than 100 ppm glycolic acid.

The hydrodehalogenation process was completed after 80 hours and the products mixture that was obtained was subjected to vacuum distillation to separate the acetic acid, after which the distillation was repeated to distil off MCAA. The product (MCAA) was collected as a colourless distillate. The colour on the Pt—Co scale was 10 units.

At the same time, 1320 g of a tar-like substance, of a content of approximately 50% MCAA, was obtained as a residue of the distillation. The ratio of the quantity of heavy residues to the quantity of product received is 0.0055.

EXAMPLE 3

A sample of the mixture used in examples 1 and 2 was subjected to a reaction with water under the same conditions as in example 2. The mass of the sample was 2000 g. Hydrolysis was also conducted for 120 minutes. The excess water was measured after this time. It was 0.51%. 64.5 g chloroacetyl chloride was measured and added to the mixture, after which it was stirred for approximately 10 minutes. The water content measured in the mixture obtained was 20 ppm. The mixture prepared in this way was then subjected to hydrodehalogenation. The conditions of the hydrodehalogenation were the same as in examples 1 and 2. The product obtained had a light yellow colour. The product did not contain GAMA or glycolic acid in quantities enabling the concentration of these impurities to be determined.

After conducting vacuum distillation to separate the excess acetic acid, the product was subjected to final vacuum distillation. The product (MCAA) was collected as a colourless distillate. The colour on the Pt—Co scale was 10 units. The liquid taken, in a quantity of 80 g was a tan-coloured mixture with a low viscosity. The MCAA content of the liquid taken was 87.5%. The ratio of the quantity of heavy residues to the quantity of product obtained was 0.01 (per waste in the form of heavy fractions of a content of 50% MCAA).

EXAMPLE 4

The mixture obtained in example 1 containing 68% MCAA, 4.5% DCAA, 21.2% acetic acid and 2.6% acetyl chloride, 1.8% chloroacetyl chloride, 1.2% acetic anhydride and 0.7% hydrogen chloride was subjected to vacuum distillation to separate the volatile fractions containing acid chlorides. The concentration of the individual chlorides and anhydrides in the mixture was determined. The acetyl chloride content was 0.2%, chloroacetyl chloride 0.4%, acetic anhydride 1.7% and HCl 0.16%. A series of four experiments in accordance with the description in example 3 were conducted using the mixture obtained. The hydrolysis stage and the reaction of the excess water with acetyl chloride were conducted such that the following concentrations of water were obtained in the mixture before hydrodehalogenation in 4 successive attempts: experiment 1—90 ppm, experiment 2—75 ppm, experiment 3—94 ppm, experiment 4—50 ppm. An ultra-pure colourless product (MCAA) was obtained after conducting the double vacuum distillation to separate the acetic acid and distil off the final product.

The invention claimed is:

1. A method of obtaining, colourless monochloroacetic acid comprising chlorination of acetic acid with chlorine in the presence of a catalyst, followed by recovery of the catalyst through vacuum distillation and purification of a remaining liquid raw product by hydrodehalogenation in the presence of a further catalyst containing metal from group X of the periodic table of elements and then vacuum distillation, wherein
   a. prior to said hydrodehalogenation, conducting a hydrolysis of the liquid raw product in order to hydrolyze anhydrides and acid chlorides present in the liquid raw product obtained after the recovery of the catalyst, at a temperature of between 50° C. to 160° C. with an overall retention time of between 30 minutes and 12 hours, whereby the hydrolysis is conducted with an excess of water, with respect to the content of acid chlorides and anhydrides, such that the concentration of water in the hydrolysed liquid raw product is between 0.05 and 5% by weight, and then
   b. the excess water from the hydrolysed liquid raw product is removed by a reaction with acid chlorides so that the concentration of water in the reaction mixture entering the hydrodehalogenation process is less than 0.01% by weight.

2. The method according to claim 1, wherein the hydrolysis of the anhydrides and acid chlorides in the liquid raw product is conducted in a reactor, an intermediate tank, or in a cascade of reactors.

3. The method according to claim 1, wherein the hydrodehalogenation is conducted by treating of the hydrolysed liquid raw product with hydrogen in the presence of said further catalyst.

4. The method according to claim 3, wherein the further catalyst is supported by/deposited on powder, granules, or extrusions of activated carbon, silica or a zeolite.

5. The method according to claim 1, wherein the hydrodehalogenation takes place in a liquid or gaseous phase.

6. The method according to claim 1, wherein the hydrodehalogenation is conducted in a liquid phase in a reactor with a fixed catalyst bed.

7. The method according to claim 1, wherein the hydrodehalogenation is conducted in a liquid phase in a circulation reactor.

8. The method according to claim 1, wherein the hydrodehalogenation is conducted in a gaseous phase in a reactor with a fixed catalyst bed.

9. The method according to claim 2, wherein the reactor or the cascade of reactors in which the hydrolysis of the anhydrides and acid chlorides is conducted, enables liquid in it to mix.

10. The method according to claim 1, wherein in step a, the concentration of water in the hydrolysed liquid raw product is within the range of 0.2 to 5% by weight.

11. The method according to claim 10, wherein in step a, the concentration of water in the hydrolysed liquid raw product is within the range of 0.3 to 0.7% by weight.

12. The method according to claim 1, wherein the hydrodehalogenation is conducted by treating of the hydrolysed liquid raw product with hydrogen in the presence of said further catalyst, and said metal from group X being palladium or platinum.

* * * * *